(12) United States Patent
Moharram et al.

(10) Patent No.: US 12,067,603 B2
(45) Date of Patent: Aug. 20, 2024

(54) ANONYMOUS LEGAL CASE INFORMATION EXCHANGE AND BIDDING PLATFORM

(71) Applicants: Tarek Moharram, London (CA); Jake A. Klassen, St. Thomas (CA)

(72) Inventors: Tarek Moharram, London (CA); Jake A. Klassen, St. Thomas (CA)

(73) Assignee: Moharram Ventures, S.A. DE C.V. (SV)

( * ) Notice: Subject to any disclaimer, the term of this patent is extended or adjusted under 35 U.S.C. 154(b) by 228 days.

(21) Appl. No.: 16/724,286

(22) Filed: Dec. 21, 2019

(65) Prior Publication Data

US 2020/0286141 A1    Sep. 10, 2020

(51) Int. Cl.

| | |
|---|---|
| *G06Q 30/00* | (2023.01) |
| *G06F 9/54* | (2006.01) |
| *G06F 21/62* | (2013.01) |
| *G06Q 10/1057* | (2023.01) |
| *G06Q 10/107* | (2023.01) |
| *G06Q 20/40* | (2012.01) |
| *G06Q 30/0601* | (2023.01) |
| *G06Q 30/08* | (2012.01) |
| *G06Q 50/18* | (2012.01) |
| *G16H 10/60* | (2018.01) |
| *H04L 9/40* | (2022.01) |

(52) U.S. Cl.
CPC ......... *G06Q 30/0611* (2013.01); *G06F 9/547* (2013.01); *G06F 21/6254* (2013.01); *G06Q 10/1057* (2013.01); *G06Q 10/107* (2013.01); *G06Q 20/401* (2013.01); *G06Q 30/0609* (2013.01); *G06Q 30/08* (2013.01); *G06Q 50/18* (2013.01); *G16H 10/60* (2018.01); *H04L 63/0421* (2013.01)

(58) Field of Classification Search
None
See application file for complete search history.

(56) References Cited

U.S. PATENT DOCUMENTS

| | | | | |
|---|---|---|---|---|
| 10,339,600 | B1 * | 7/2019 | Lieberman | H04L 67/34 |
| 2015/0339764 | A1 * | 11/2015 | Roychowdhury | G16H 40/20 705/2 |
| 2017/0032461 | A1 * | 2/2017 | Zheng | G06Q 40/04 |
| 2017/0374502 | A1 * | 12/2017 | Gabel | G06Q 50/26 |
| 2018/0268370 | A1 * | 9/2018 | Fallah | H04L 63/0428 |

* cited by examiner

*Primary Examiner* — Mila Airapetian
(74) *Attorney, Agent, or Firm* — Klarquist Sparkman, LLP

(57) ABSTRACT

Methods and systems for communication between members of the general public and practicing legal services professionals by way of an initially-anonymous, secure, online platform. The members of the general public upload certain personal information concerning a legal matter to the platform through an electronic device, which is validated and anonymously posted for viewing by practicing legal services professionals. The practicing legal services professionals review the posted information and may express interest, in an anonymous way through the platform, in offering legal services to the members of the general public who posted information concerning a legal matter. Identifying information is only shared once a member of the general public accepts an offer of legal services.

9 Claims, No Drawings

ANONYMOUS LEGAL CASE INFORMATION EXCHANGE AND BIDDING PLATFORM

FIELD OF THE INVENTION

The present invention relates to an initially-anonymous, secure, online platform through which potential causes of legal action are posted (without specific identifying information), reviewed, bid upon, and eventually awarded to a bidding party.

BACKGROUND

The search for representation within the existing framework of the legal marketplace can be generally described by the following series of events/steps:

A person experiences some type of unexpected/unwanted event (including but not limited to a(n) car accident, assault, adverse drug reaction, financial loss, etc.).

As a result of the unexpected/unwanted event, the person now has a potential cause of legal action (hereinafter referred to as "case(s)") against the entity/entities responsible for/contributing to the occurrence/severity of the event.

If the person elects to pursue legal action, he/she must then begin manually searching for one/more legal professionals based in large measure (if not exclusively) upon: 1) the effectiveness of each firm's/individual's marketing campaign; 2) referrals from family members, friends, and/or colleagues; and/or 3) the results of one/more online searches).

After selecting one/more individuals/firms with whom to begin exploring the prospect of creating a relationship, the person must now manually contact each party (predominantly be telephone, e-mail, or website-based contact form). In this process, he/she will be forced to tell what might be a traumatic, and therefore emotionally-sensitive, story to each party over and over again.

The party at the other end of the person's communication will then begin a conflict of interest check, which will often take at least a couple of business days.

Once the conflict of interest checks have been completed, certain parties may be disqualified from representing the person. Those that have not been disqualified due to conflict of interest will schedule an initial consultation with the person which will almost exclusively be held at the office of each responding party.

The person must then re-arrange their existing work and/or personal scheduled) in order to accommodate each responding party's scheduled office hours and availability.

Assuming the person's schedule shares some common availability with that of each party, the person must then physically travel to each party's office for an in-person initial consultation.

During the meeting with each party, the person must once again re-tell his/her potentially painful story.

After hearing the person's story, the listening petty will either express an interest in taking on the case or decline to be involved any further.

In the latter circumstance, the person has just wasted a significant amount of time and effort. He/she must now decide whether to continue the search by starting this process all over again or simply abandon his/her quest for justice.

In the former circumstance, the party will tell the person the terms and conditions upon which their relationship will be based. In many situations, there is no negotiation between the person and the party; both because of the significant disparity in perceived power between the person and the party and because the person likely has no information upon which to base his/her decision about the terms being fait/unfair or favorable/unfavourable. The person must now decide whether, after all of these steps and delays, to decline a set of terms with which he/she may be uncomfortable or simply accept them as the least negative available option.

Aside from the negative impact(s) that the existing paradigm has upon individuals seeking legal representation, parties that provide legal services also suffer from the striking inefficiencies of this marketplace's current information-sharing capacity.

Parties dial compete for clients within this marketplace are forced to invest heavily in their respective advertising budgets in an attempt to out-spend the field and therefore build the strongest levels of consumer brand recognition. Unlike many other types of marketplace, where service providers can guarantee customer satisfaction by promising a specific result, claim to be 'the best', and/or use pest outcomes as an indicator for future success, this industry's rules of professional responsibility significantly restrict the messaging that would otherwise be available. Thus, the resulting advertising campaigns frequently resort to simply inundating the target market with materials and then focusing the messaging on trusting the name(s) a consumer might recognize because of the past/current volume of activity.

SUMMARY OF THE INVENTION

The present invention (hereinafter "Invented Platform") is comprised of both a method and a system. The method which may permit members of the general public (hereinafter "Clients") to access the Invented Platform through an electronic device, have certain Client Personal Information (including, but not limited to, device IP address, partial postal/zip code, e-mail address. Transportation Registration Number, and/or geolocation) validated, anonymously post information about their case (including, but not limited to, the date, time, environmental circumstances which existed, any other individuals present, and any other contributing/relevant factors; hereinafter "Case Information") for viewing by practicing legal services professionals (hereinafter "Practitioner(s)"), review and accept anonymous bids from Practitioner(s), and then have access to the contact information associated with the Practitioner(s) whose bid(s) were accepted; the method which may also permit Practitioners to access the Invented Platform through an electronic device, have certain Practitioner Personal Information (including, but not limited to, name, contact information, picture, professional registration number, payment information, device IP address, and/or geolocation) validated, review the posted cases, acquire bids, anonymously apply them to cases of interest along with their proposed fee arrangement and other terms (hereinafter "Bid Information"), be notified of bids where were accepted by Clients, and to have access to the contact information of the Client(s) who accepted the bid(s).

The system which may be operatic through both Client and Practitioner devices connecting to and exchanging information with a Web Server and/or an API Server to gam access to the Invented Platform, either of which may in dim connect to and exchange information with a network of databases, geolocation APIs, reCAPTCHA widgets. Transportation Registration Number Databases, Practitioner Professional Registration Number Databases, Payment Recessing Platforms, Typing Biometrics APIs, and/or E-Mail Communications Platforms for validation purposes, and either of which may in turn connect to and exchange information with Case Information Entry Platforms to generate and display posted cases, and which may in turn connect to and exchange information with a Payment Processing Platforms for managing bid acquisition transactions, which may in him again connect to and exchange information with the Client and/or Practitioner devices to permit bid application, bid review, and bid acceptance, which may in turn connect to and exchange information with E-Mail Communications Platforms to transmit case, bid, and/or contact information upon bid acceptance.

The Invented Platform, through its novel method and system, addresses several needs which are not currently being adequately met in the marketplace (whether virtually or through traditional, in-person settings). Since the Practitioner information exchanged through Invented Platform is anonymous until after bid acceptance, Clients are now able to take control of their search for legal representation by having Practitioners compete for their business based only on professional merit and offer competitiveness. Moreover, it is critical to also ensure Client anonymity because of the sensitive nature of the information needed to describe many types of Client cases. For instance, a Client seeking Practitioner representation related to a challenging health condition or stemming from an instance of alleged abuse is understandably keen to prevent this underlying case information from being made public unnecessarily (especially if the case information which is shared relates to and/or is connected with that Client's personal identifying information). While this need Client for anonymity creates a challenge, the solution is built into the method and system through which the Invented Platform operates. The Invented Platform balances the need for Client anonymity with the need to protect against malicious, repeated, automated, and/or fraudulent case postings through the application of a network of interconnected steps and systems to significantly mitigate the prospects such harmful activity. In order to accomplish this goal, the Invented Platform may exchange various types of Client Personal Information, Case Information, Practitioner Personal information, and/or Bid Information for various types of 'tokens' to drastically mitigate any privacy/data security rides by detaching (to some degree) said various types of sensitive information from said tokens and by storing said information and tokens in a decentralized manner. Finally, the Invented Platform makes finding a Practitioner much more convenient and cost-effective by drastically reducing the amount of 'leg work' required by the traditional method of finding and retaining a Practitioner.

This revolution in the legal marketplace also empowers Practitioners to put less emphasis on investing in high-saturation marketing campaigns in order to simply keep-up with one's competitors. By using the Invented Platform, smaller Practitioner firms and new/solo Practitioners have a much more balanced opportunity to compete for Clients in spite of the fact that they have fewer financial resources that the larger entities in the legal services marketplace. Instead of having to rely solely on marketing expenditures, such smaller/newer Practitioners can now be considered without having as much emphasis placed upon things like office appearance/amenities, organizational branding materials, and name recognition. Practitioners in the legal services marketplace may also benefit from having access to the so-called 'big data' that is captured, collected, and stored through the operation of the Invented Platform.

DESCRIPTION OF THE INVENTION

The process of the Invented Platform method is described below step-by-step in order to illustrate the preferred embodiment of the method. This breakdown of each user's path through using Invented Platform is not intended to exclude other possible embodiments, it is merely a description of the preferred embodiment.

There are two possible paths that a user of Invented Platform can take; Client or Practitioner. In either case, a Client or Practitioner user will use an electronic device, such as a computer, smartphone, tablet, or other network-connected electronic device, to communicate with Invented Platform servers, via a website, downloadable software application, or other suitable user interface, to carry out the steps of the present method. The information transmitted by a Client or Practitioner user is preferably transmitted via the Internet, bat may be transmitted via other communication networks, such as cellular networks, and is received by the Invented Platform servers, where it is stored, processed, and displayed, as described below.

On the Client Path, the Client will first visit the landing page for Invented Platform. There may be several opportunities on the landing page for the Client to sign-up to use the service. The landing page may also contain one or mote video(s) that explain the service being provided, user testimonials, and step-by-step instructions for how the Client will interact with Invented Platform and corresponding explanations.

Should the Client elect to sign-up by clicking one of these buttons, he/she may be redirected to the Invented Platform Terms of Service. Clients may only begin using the Invented Platform once they have reviewed and consented to be bound by the Terms of Service. The Terms of Service may include an explanation that each Client is responsible to ensure that he/she does not post identifying personal information on the platform and dial a failure to do so will not result in liability for Invented Platform, a disclosure that posting case information may result in a waiver of any Practitioner-client privilege, and other important terms. The Client may also be presented with the invented Platform Privacy Policy for review and acceptance.

Upon accepting the Invented Platform Terms of Service and Privacy Policy, the Client may be redirected to another page whereon he/she may select which type of user he/she happens to be (in this case, the Client will select a button that says/represents 'Client').

Following this step, the Client may be prompted to enter the first 3-5 characters of his/her postal/zip code and/or his/her Driver's License number. This data will be used to verify that the Client is a real person and dial he/she in fact resides within the geographic areas within which the Invented Platform operates. The Client may also be validated through other means, including but not limited to rate limiting of data entry and/or signup attempts, IP address validation, and geolocation queries and validation.

At this point, the Client may be given an opportunity to enter information about his/her potential cause of legal action. There may also be a dropdown menu that will allow the user to classify the type of event (for instance, car accident, physical assault, slip/trip-and-fall, long-term disability claim, etc.). This section of Invented Platform may also allow the Client to utilize drop-down menus, textboxes, and other data entry fields/tools in order to explain the circumstances that surround his/her intent to pursue legal action. Said fields may include the date on which the event took place, the number of people involved, the estimated amount of damages, the nature and extent of any injuries sustained, and/or a blank textbox for a brief summary of the event in question. The Client may either complete this data entry process entirely during a single session or save initial progress for completion at some other time.

Once the Client has described his/her potential cause of action by entering data into the available fields, he/she may click a button to authorize the publication of the data on the Invented Platform.

The Client will then receive his/her unique login information, consisting of a randomly-generated username and a randomly-generated password. This may be the only login information through which the Client may access his/her profile. In the event that the Client loses these unique, randomly-generated credentials, he/she may be unable to access his/her profile and may be forced to create a new profile which may randomly-generate new login credentials.

After posting, Clients may be able to view the bids submitted by Practitioners. Each bid may include two types of information: 1) general information about the Practitioner that is independent from the details of the case being bid upon ("Practitioner Personal Information"); and 2) specific information that relates to the case being bid upon ("Bid Information")

The former type of information may include the Practitioner's areas of subject matter expertise (personal injury, medical malpractice, etc.), special certifications/designations, the number of years that the Practitioner has been licensed to practice, the number of years during which the Practitioner has actually practiced, the size of the Practitioner's firm, and/or other relevant objective information.

The letter type of information may include the Practitioner's proposed fees and the other terms that would govern the relationship between Practitioner and Client, should Practitioner be selected to represent the Client in relation to the case being bid upon. None of the information, general or specific, may include details that identify the Practitioner or the Practitioner's firm, either directly by name or contact details, or indirectly by suggestion or implication.

Clients may not be able to see any other information about the bidding Practitioners at this stage (i.e., no Practitioner/firm name, address, telephone number, e-mail address, Practitioner professional registration number, picture, etc.). Clients are therefore able to review the bidders based upon their merit and the competitiveness of their offer.

Once the Client has selected the most suitable offer submitted to him/her by one of the bidding Practitioners, he/she may enter his/her e-mail address in order to accept the bid. Doing so may cause the relevant case information to be automatically sent to both the selected Practitioner and the Client, along with the relevant bid details, and the contact information for each party. This information transfer being complete, the Client's detailed case information may be deleted along with the Client's profile. The non-specific Client case data (type of case, estimation of the coat of damages, list of injuries sustained, number of people involved, etc.) may be retained for so-called 'big data' purposes within a mass database, created by compiling the all of the submitted case data from every Client.

On the Practitioner Path, the Practitioner may begin by interacting with the same landing page described above, in paragraph [0023], which may also contain information for Practitioners about the Invented Platform, how to sign-up, and other relevant information.

Should the Practitioner elect to sign-up by selecting one of the associated buttons on the landing page, the Practitioner may also be redirected to the Terms of Service and Privacy Policy, described above in paragraph [0022], which may also contain information for Practitioners on topics which may include, but are not limited to, an explanation of the requirement to enter the requested information to the best of his/her ability, a statement that Practitioners must refrain from attempting to circumvent the initial anonymity of the bidding process, and an acknowledgement that Practitioners may be penalized by the platform for repeatedly under-bidding on Client cases only to later renege once contact with the Client has been established. As before, Practitioners may only begin using the Invented Platform once they have reviewed and consented to be bound by the Terms of Service and Privacy Policy.

After consenting to the Terms of Service and Privacy Policy, the Practitioner may also receive a set of randomly-generated login credentials, as described above in paragraph [0025]. Alternatively, the Practitioner may elect to utilize a so-called 'social sign-in' or may simply create a personalized username and password.

The Practitioner may now begin entering his/her information such as first name, last name, firm name (if applicable), business address, telephone number, e-mail address. Practitioner Professional Registration Number, years of professional experience, areas of subject matter expertise, special certifications/designations, geographical area within which the Practitioner is interested in practicing, and other relevant objective information. Certain information, such as the Practitioner's Professional Registration Number, may be automatically checked by the platform to ensure that he/she is licensed to practice as a Practitioner and/or that his/her license to practice is active. Other tools to validate the Practitioner's identity may be used.

Once the Practitioner has created a profile, he/she may now be able to view Client cases. Using Invented Platform's platform will enable Practitioners to access, review, evaluate, and select Client cases of interest, posted by Clients. Either through the platform's case search tool(s) (such as by date, type, amount of estimated damages, etc.) or simply by manually reviewing each posted case, Practitioners will no longer have to invest the resources required by the traditional paradigm of scheduling individual 30- to 60-minute initial consultations with each Client in order to evaluate their case and decide whether or not to represent each Client in question.

The Practitioner may then purchase bids as a means of expressing his/her interest in one/more case(s). Bid purchasing may either be accomplished by purchasing a single bid to apply to a case of interest at the time of identification or purchased in bulk beforehand and then later applied to cases of interest as they are identified by the Practitioner. Bid prices may be established by Invented Platform and amended from time to time.

In order to complete the bidding process for one/more case(s), the Practitioner must not only apply a bid to each of the cases of interest, but he/she must also include an offer, indicating the terms under which he/she would be willing to lake the case(s) in question. Said terms may include the proposed hourly rate/contingency fee, the terms related to processing the costs related to the case (filing fees, printing, postage, etc.), changes in hourly rate and/or contingent fee based upon the chronological progression of the case from beginning to end, and other important terms (hereinafter "Bid Information").

Once the Practitioner has bid on at least one case, his/her active bids may be displayed on a separate page that may list each bid, the proposed terms, the date on which the Practitioner placed the bid, whether or not the Client associated with the case has viewed the bid, whether the case has been awarded to another Practitioner, and other relevant information.

In the event that the Practitioner's bid is accepted by the Client associated with the bid-upon case, the information exchange described above, m paragraph [0034] may occur. Thereafter the Client and Practitioner may contact each other to proceed with the case, as agreed.

The components (and their relationships to one another) of the Invented Platform's system is described below step-by-step in order to illustrate the preferred embodiment of the method. This breakdown of each user's path through using Invented Platform is not intended to exclude other possible embodiments, it is merely a description of the preferred embodiment.

The system which may be operable through both Client and Practitioner devices connecting to and exchanging information with a Web Server and/or an API Server to gain access to the Invented Platform, either of which may in turn connect to and exchange information with a network of databases, geolocation APIs, reCAPTCHA APIs, Transportation Registration Number Databases, Practitioner Professional Registration Number Databases, Payment Processing Platforms, Typing Biometrics APIs, and/or E-Mail Communications Platforms for validation purposes, and either of which may in turn connect to and exchange information with Case Information Entry Platforms to generate and display posted cases, and which may in turn connect to and exchange information with a Payment Processing Platforms for managing bid acquisition transactions, which may in turn again connect to and exchange information with the Client and/or Practitioner devices to permit bid application, bid review, and bid acceptance, which may in turn connect to and exchange information with E-Mail Communications Platforms to transmit case, bid, and/or contact information upon bid acceptance.

The present invention has been described with reference to an exemplary embodiment, however, it will be understood by those skilled in the art that various changes may be made and equivalents may be substituted for elements thereof without departing from the scope of the invention as set out herein. Therefore, it is intended that the invention not be limited to the particular embodiments disclosed herein.

The invention claimed is:

1. A system for facilitating initially-anonymous, yet validated and secure, connections between Clients and Practitioners, comprising:

A Client device which connects to and exchanges Client Personal Information and Case Information with a Web Server, and an API Server, and an Invented Platform and its associated databases, and Verification APIs, widgets, and databases, and a Case Information Entry Platform, and an E-mail Communications Platform, for the purpose of downloading, gaining access to, and interacting with the Invented Platform, and its associated databases, and validating, transmitting, and storing said Client Personal Information and Case Information;

Said Web Server which connects to and exchanges said Client Personal Information and Case Information with said Client device, said Case Information Entry Platform, and said E-Mail Communications Platform for the purpose of downloading, gaining access to, and interacting with the Invented Platform, permitting the posting of Client Cases, and transmitting Client Personal Information to a Practitioner Device via an E-mail Communications Platform;

Said API Server which connects to and exchanges said Client Personal Information and Case Information with said Client device, Verification APIs, Widgets, and Databases, and said Invented Platform Databases for the purpose of downloading, gaining access to, and interacting with the Invented Platform and its associated databases, validating said Client Personal Information and Case Information, and storing said Client Personal Information and Case Information;

Said Verification APIs, widgets, and databases which connect to and exchange Client Personal Information with said Client device and said Invented Platform Databases via the API Server for the purpose of Client Personal Information and Case Information validation and storage;

Said Invented Platform databases which connects to and exchanges said Client Personal Information and Case Information with said Client device and Verification APIs, widgets, and databases via the API Server for the purpose of Client validation and storage;

Said Case Information Entry Platform which connects to and exchanges said Client Personal Information and Case Information with said Client Device via said Web Server, and with said Verification APIs, widgets, and databases, and said Invented Platform Databases via said API Server; and Said E-Mail Communications Platform which connects to and exchanges said Client Personal Information with said Client device and Practitioner device via said Web Server for the purpose of sharing said Client Personal Information, wherein the Client device sends a case type request to the Case Information Entry Platform via the Web Server and sends it back to the Client device, permitting Client to enter their Case Information, send said Case Information back to Case Information Entry Platform, which then returns a Form ID number, a signup token, and partial postal/zip code to API Server.

2. The system of claim 1 wherein the means through which the Client device sends a request for, and later receives, the Invented Platform application data is selected from the group consisting of: a Web Browser, an App Store, or some combination of the members of this group.

3. The system of claim 1 wherein the Client Personal Information and Case Information which is to be validated by sending from the Client device via the API Server to the Validation APIs, Widgets, and Databases and Invented Platform Databases is selected from the group consisting of: Client device IP address, partial Client device postal code, partial Client postal code, a reCAPTCHA code from the widget downloaded to Client device, Client Transportation Registration Number, e-mail address, geolocation, Client Typing Biometrics, or some combination of the members of this group.

4. The system of claim 1 wherein the Client Personal Information and Case Information which is to be validated is sent from the Client device via the API Server to the Validation APIs, Widgets, and Databases and Invented Platform Databases which are selected from the group consisting of: a Geocoder API, a Transportation Registration Number Database, the Invented Platform Database A for rate limiting, an Information Protocol Stack, or some combination of the members of this group.

5. The system of claim 1 wherein Case Information which is entered into the Case Information Entry Platform is selected from a group consisting of: date, time, location, conditions at the scene (including visibility, temperature, lighting, and weather), the type of footwear Client was wearing at the time, the safety signage present, the injuries sustained, the level of medical attention received, the duration of receiving medical attention, the number of days which separated the onset of the circumstances and the receipt of medical attention, whether or not time at work was missed as a result of the circumstances, the amount of work time missed, the nature of Client's occupation, Client's average annual salary, Client's highest level of education attained, Client's age, the non-healthcare damages experienced by Client, make, model, and year of Client's vehicle, whether or not Client was found at-fault, whether or not Client was intoxicated, how many people were involved in the circumstances, whether they remained at the scene, whether there were witness accounts, whether Client has pre-existing injuries and (if so) what they are, whether Client has long-term disability coverage, whether or not Client has a copy of their employment contract, and a free-form request for other information which is relevant to the circumstances, or some combination of the members of this group.

6. The system of claim 1 wherein the API Server, upon each Client device sign in or refresh that triggers a request, sends the Client device information about any Practitioner bids which may have been applied to Client's posted case and which allows Client to accept a Practitioner bid and, upon this taking place, sends bid acceptance data to the API Server.

7. The system of claim 1 wherein the Client device prompts Client to send that Client's e-mail address to the Web Server, which then sends said e-mail address to E-Mail Communications Platform, which then sends a notification e-mail to the Practitioner device which placed the bid that was accepted by the Client device.

8. The system of claim 1 wherein the API Server sends the Practitioner Personal Information which is associated with the accepted bid to the Client device and displays it thereon.

9. A system for facilitating initially-anonymous, yet validated and secure, connections between Clients and Practitioners, comprising:

A Client device which connects to and exchanges Client Personal Information and Case Information with a Web Server, and an API Server, and an Invented Platform and its associated databases, and Verification APIs, widgets, and databases, and a Case Information Entry Platform, and an E-mail Communications Platform, for the purpose of downloading, gaining access to, and interacting with the Invented Platform, and its associated databases, and validating, transmitting, and storing said Client Personal Information and Case Information;

Said Web Server which connects to and exchanges said Client Personal Information and Case Information with said Client device, said Case Information Entry Platform, and said E-Mail Communications Platform for the purpose of downloading, gaining access to, and interacting with the Invented Platform, permitting the posting of Client Cases, and transmitting Client Personal Information to a Practitioner Device via an E-mail Communications Platform;

Said API Server which connects to and exchanges said Client Personal Information and Case Information with said Client device, Verification APIs, Widgets, and Databases, and said Invented Platform Databases for the purpose of downloading, gaining access to, and interacting with the Invented Platform and its associated databases, validating said Client Personal Information and Case Information, and storing said Client Personal Information and Case Information;

Said Verification APIs, widgets, and databases which connect to and exchange Client Personal Information with said Client device and said Invented Platform Databases via the API Server for the purpose of Client Personal Information and Case Information validation and storage;

Said Invented Platform databases which connects to and exchanges said Client Personal Information and Case Information with said Client device and Verification APIs, widgets, and databases via the API Server for the purpose of Client validation and storage;

Said Case Information Entry Platform which connects to and exchanges said Client Personal Information and Case Information with said Client Device via said Web Server, and with said Verification APIs, widgets, and databases, and said Invented Platform Databases via said API Server; and Said E-Mail Communications Platform which connects to and exchanges said Client Personal Information with said Client device and Practitioner device via said Web Server for the purpose of sharing said Client Personal Information, wherein the API Server verifies said signup token which was housed on the Client device, sends said partial Client device postal/zip code information to Database A for validation and, upon validation from Database A, sends the Client device notice of validation, validates Form ID number, and validates Client device IP address through a query to Internet Protocol Stack and, upon successful validation, generates a random Client username and password through using a Key Derivation Function (KDF), sends said data to the Client device, generates an access token, saves latitude and longitude associated with case ID, and sends a notification to the Client device that case is now active.

* * * * *